(12) United States Patent
Miller et al.

(10) Patent No.: US 6,274,160 B1
(45) Date of Patent: Aug. 14, 2001

(54) METHODS OF USE OF HISTAMINE $H_2$ AGONISTS IN TREATING DRY EYE

(75) Inventors: Steven T. Miller; Daniel A. Gamache, both of Arlington; John M. Yanni, Burleson, all of TX (US)

(73) Assignee: Alcon Laboratories, Inc., Fort Worth, TX (US)

(*) Notice: Subject to any disclaimer, the term of this patent is extended or adjusted under 35 U.S.C. 154(b) by 0 days.

(21) Appl. No.: 09/529,837

(22) PCT Filed: Oct. 20, 1998

(86) PCT No.: PCT/US98/22144
§ 371 Date: Apr. 19, 2000
§ 102(e) Date: Apr. 19, 2000

(87) PCT Pub. No.: WO99/20265
PCT Pub. Date: Apr. 29, 1999

Related U.S. Application Data
(60) Provisional application No. 60/062,906, filed on Oct. 21, 1997.

(51) Int. Cl.$^7$ ............................................. A61K 9/06
(52) U.S. Cl. ..................... 424/427; 514/887; 514/944
(58) Field of Search ............................ 514/914, 887, 514/944; 424/78.04, 78.05, 427

(56) References Cited

U.S. PATENT DOCUMENTS

| | | | |
|---|---|---|---|
| 3,991,759 | 11/1976 | Urquhart | 128/260 |
| 4,131,651 | 12/1978 | Shah et al. | 424/78 |
| 4,315,024 | 2/1982 | Abelson | 424/273 |
| 4,370,325 | 1/1983 | Packman | 424/245 |
| 4,409,205 | 10/1983 | Shively | 424/78 |
| 4,744,980 | 5/1988 | Holly | 424/78 |
| 4,818,537 | 4/1989 | Guo | 424/427 |
| 4,883,658 | 11/1989 | Holly | 424/80 |
| 4,914,088 | 4/1990 | Glonek et al. | 514/76 |
| 4,966,773 | 10/1990 | Gressel et al. | 424/489 |
| 5,041,434 | 8/1991 | Lubkin | 514/182 |
| 5,075,104 | 12/1991 | Gressel et al. | 424/78.04 |
| 5,290,572 | 3/1994 | MacKeen | 424/602 |
| 5,294,433 | 3/1994 | Singer et al. | 424/52 |
| 5,294,607 | 3/1994 | Glonek et al. | 514/76 |
| 5,403,841 | 4/1995 | Lang et al. | 514/226.8 |
| 5,869,479 | * 2/1999 | Kreuter et al. | 514/212 |

FOREIGN PATENT DOCUMENTS

WO 94/04120    3/1994    (WO).

OTHER PUBLICATIONS

Abelson, et al., $H_2$–Receptors in the Human Ocular Surface, *Arch Ophthalmol*, vol. 99, pp. 302–304 (1981).

Dilly et al., Surface Changes in the Anaesthetic Conjunctiva in Man, with Special Reference to the Production of Mucus from a Non–Goblet–Cell Source, *British Journal Ophthalmology*, vol. 65, pp. 833–842 (1981).

Fukuda et al., Histamine $H_2$ receptor mediates keratan sulfate secretion in rabbit chondrocytes: role of cAMP, *American Physiological Society*, pp. C1653–C1657 (1993).

(List continued on next page.)

*Primary Examiner*—Thurman K. Page
*Assistant Examiner*—Liliana Di Nola -Baron
(74) *Attorney, Agent, or Firm*—Michael C. Mayo; Patrick M. Ryan

(57) ABSTRACT

A topical ophthalmic composition for the treatment of dry eye in humans, comprising one or more histamine $H_2$ agonists, is disclosed.

4 Claims, 1 Drawing Sheet

OTHER PUBLICATIONS

Figure 1:
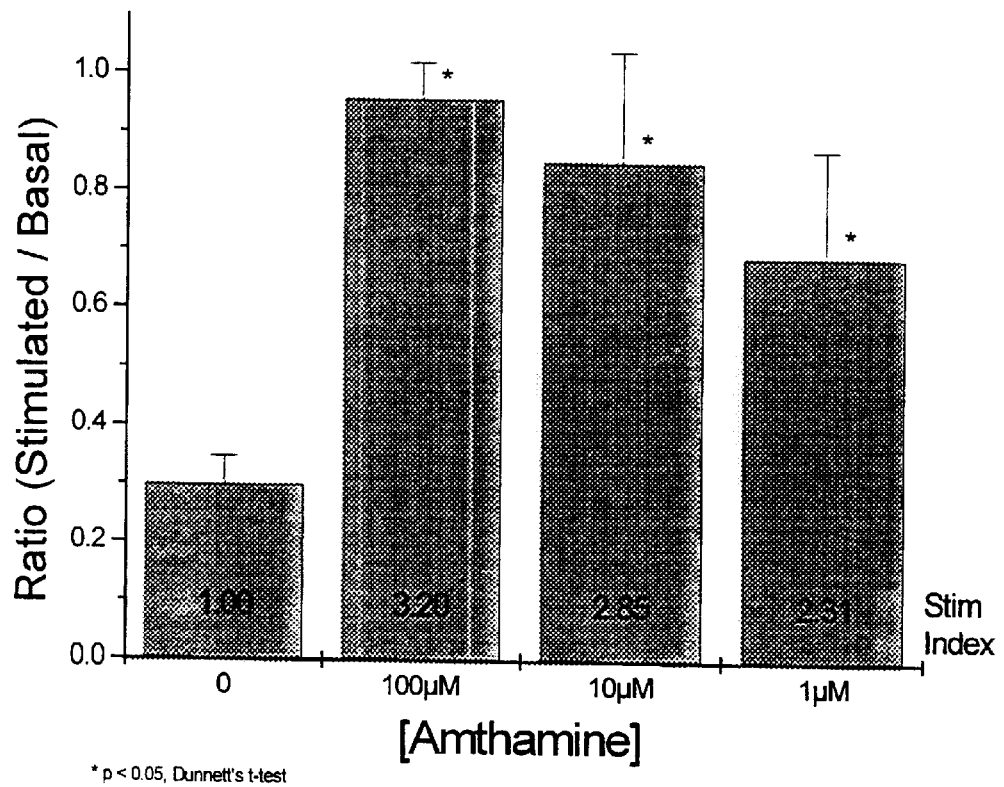

Greiner et al., Mucus Secretory Vesicles in Conjunctival Epithelial Cells of Wearers of Contact Lenses, *Archives of Ophthalmology,* vol. 98, pp. 1843–1846 (1980).

Kaliner et al., Human respiratory mucus, *J. Allergy Clin. Immunol.,* vol. 73, No. 3, pp. 318–323 (1984).

Kohno et al., Dimaprit, a Histamine $H_2$–Agonist, Inhibits Anaphylactic Histamine Release from Mast Cells and the Decreased Release Is Restored by Thioperamide ($H_3$–Antagonist), but Not by Cimetidine ($H_2$–Antagonist), *Japan J. Pharmacol.,* vol. 62, pp. 75–79 (1993).

Lemp, Report of the Nation Eye Institute/Industry Workshop on Clinical Trials in Dry Eyes, *The CLAO Journal,* vol. 21, No. 4, pp. 221–231 (1995).

Sharif, et al., Emedastine: A Potent, High Affinity Histamine $H_1$–Receptor–Selective Antagonist for Ocular Use: Receptor Binding and Second Messenger Studies, *Journal of Ocular Pharmacology,* vol. 10, No. 4, pp. 653–664 (1994).

Shelhammer et al., Immunologic and Neuropharmacologic Stimulation of Mucus Glycoprotein Release from Human Airways In Vitro, *J. Clin. Invest.,* vol. 66, pp. 1400–1408 (1980).

Watanabe et al., Human Corneal and Conjunctival Epithelia Produce a Mucin–Like Glycoprotein for the Apical Surface, *Investigative Ophthalmology and Visual Science,* vol. 36, No. 2, pp. 337–344 (1995).

\* cited by examiner

METHODS OF USE OF HISTAMINE $H_2$ AGONISTS IN TREATING DRY EYE

This application is the national stage of PCT/US98/22144, filed Oct. 20, 1998, which claims benefit of provisional application No. 60/062,906, filed Oct. 21, 1997.

The present invention is directed to compositions containing histamine $H_2$ agonists and methods for their use in treating dry eye. The $H_2$ agonists of the present invention stimulate the release of mucins in the eye. The invention is also directed to methods of preventing and treating dry eye with the compositions of the present invention.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, corneal damage may occur leading to impaired vision. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, Report of the Nation Eye Institute/Industry Workshop on Clinical Trials in Dry Eyes, *The CLAO Journal,* volume 21, number 4, pages 221–231 (1995)).

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et a l.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.) and U.S. Pat. No. 5,294,607 (Glonek et al.).

U.S. Pat. No. 3,991,759 (Urquhart) is directed to the use of ocular inserts in the treatment of dry eye. Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate preocular tear film; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer. Therapeutics which promote the production of endogenous tear components, such as mucins, will meet these needs.

Mucins are proteins which are heavily glycosylated. Mucins provide protective and lubricating effects to epithelial cells, especially those of mucosal membranes. Mucins have been shown to be secreted by vesicles and discharged on the surface of the conjunctival epithelium of human eyes (Greiner et al., Mucus Secretory Vesicles in Conjunctival Epithelial Cells of Wearers of Contact Lenses, *Archives of Ophthalmology,* volume 98, pages 1843–1846 (1980); and Dilly et al., Surface Changes in the Anaesthetic Conjunctiva in Man, with Special Reference to the Production of Mucus from a Non-Goblet-Cell Source, *British Journal of Ophthalmology,* volume 65, pages 833–842 (1981)). A number of human-derived mucins which reside in the apical and subapical corneal epithelium have been isolated and cloned (Watanabe et al., Human Corneal and Conjunctival Epithelia Produce a Mucin-Like Glycoprotein for the Apical Surface, *Investigative Ophthalmology and Visual Science,* volume 36, number 2, pages 337–344 (1995)). Recently, Watanabe discovered a new mucin which is secreted via the cornea apical and subapical cells as well as the conjunctival epithelium of the human eye (Watanabe et al., *IOVS,* volume 36, number 2, pages 337–344 (1995)). These mucins provide lubrication, and additionally attract and hold moisture and sebaceous material for lubrication and the corneal refraction of light. Nowhere in the art, however, has the use of histamine $H_2$ agonists been proposed to stimulate mucin production in ocular tissues as a treatment for dry eye.

SUMMARY OF THE INVENTION

The present invention is directed to compositions and methods for the treatment of dry eye. More specifically, the present invention discloses ophthalmic compositions containing histamine $H_2$ agonists and methods for treating dry eye.

The $H_2$ agonists work by increasing mucin production and secretion from ocular surface epithelial cells of the cornea and conjunctiva. The increased mucin provides the base level of lubricant and aqueous attractant to provide the necessary layer of tear fluid. The increased production of tear fluid lubricates the surface of the eye and prevents the symptoms associated with dry eye.

DETAILED DESCRIPTION OF THE INVENTION

It has now been discovered that histamine $H_2$ agonists stimulate mucin production in conjunctival epithelium and are therefore believed to be useful in treating dry eye. As used herein, the terms "histamine $H_2$ agonists" or "$H_2$ agonists" refer to those molecules which stimulate $H_2$ receptors of the ocular surface, evoking mucin release.

The present invention contemplates all known and yet to be discovered $H_2$ agonists. Examples of $H_2$ agonists of the present invention include dimaprit, amthamine and impromidine. The most preferred $H_2$ agonist of the present invention is dimaprit.

The histamine $H_2$ agonists of the present invention are available from numerous sources. For example, the $H_2$ agonists may be obtained from Sigma Chemical (St. Louis, Mo.), Research Biochemicals International (Natick, Mass.) and Biomol (Plymouth Meeting, Pa.). As stated above, other $H_2$ agonists may become available through discovery, and these molecules and their methods of discovery and preparation are also contemplated by the present invention. In particular, the $H_2$ agonists of the present invention may be elucidated by various receptor based biological assays. For example, Sharif, et al., Emedastine: A Potent, High Affinity Histamine $H_1$-Receptor-Selective Antagonist for Ocular Use: Receptor Binding and Second Messenger Studies, *Journal of Ocular Pharmacology,* volume 10, no. 4, pages 653–664 (1994) describes a method wherein the affinity of molecules for histamine $H_1$, $H_2$ and $H_3$ receptors can be determined.

EXAMPLE 1

The mucin secreting efficacy of $H_2$ agonists of the present invention may be tested with the following assay:

Conjunctival tissue, human conjunctival tissue from postmortem tissue donors obtained within 8 hours of death by various eye banks and transported in Dexsol® corneal preservation medium or inferior palpebral to inferior bulbar excised from rats, is first obtained. Conjunctival tissue samples are then randomized and placed in buffer for mucin secretion. Basal release (i.e., control, no chemical stimulus) samples of each tissue are collected after thirty minutes. The tissues are then transferred to buffer with or without stimulus. The activated tissues are stimulated with potential secretagogues such as various $H_2$ agonists. Stimulated and unstimulated release samples are then collected after thirty minutes. The collected samples are coated in replicate wells of microtiter plates. Coated wells are then blocked and probed with a FITC conjugated lectin (*Helix pomatia* agglutinin) specific for terminal N-acetylgalactosamine residues of glycoprotein samples (e.g., mucins). The microtiter plates are then read in a fluorescence plate reader. The resultant fluorescence data is interpolated from a standard curve generated concurrently using (1) (bovine submaxillary gland mucin). Mucin values from stimulated release samples are then normalized by dividing each with its matched basal release control. The resultant ratio of stimulated:basal levels of mucin is then used to compare treatment groups to controls groups.

EXAMPLE 2

Amthamine, an $H_2$ agonist of the present invention, was tested in the in vitro mucin secretion assay described in Example 1, above. The efficacy of amthamine is illustrated in Table 1, as a ratio of the amount of mucin released from $H_2$ agonist stimulated samples versus the amount of mucin released from control samples. These data are also illustrated in FIG. 1, where the stimulate index is the ratio of $H_2$ agonist stimulated value versus the control value.

TABLE 1

Effects of amthamine on the release of mucins from rat conjuctival cells

| Amthamine ($\mu$M) | Ratio (Stimulated:Basal) mucin release |
|---|---|
| control | 0.30 ± 0.05 |
| 1.0 | 0.69 ± 0.18 |
| 10.0 | 0.85 ± 0.19 |
| 100.0 | 0.96 ± 0.06 |

The histamine $H_2$ agonists of the present invention are intended for administration to a human patient suffering from dry eye. Preferably, the histamine $H_2$ agonists of the present invention will be administered topically.

The histamine $H_2$ agonists of the present invention may be contained in various types of pharmaceutical compositions, in accordance with formulation techniques known to those skilled in the art. In general, the histamine $H_2$ agonists will be formulated in solutions for topical ophthalmic administration. Solutions, suspensions and other dosage forms are particularly preferred for the treatment of dry eye.

The ophthalmic compositions of the present invention will include one or more histamine $H_2$ agonist(s) in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the histamine $H_2$ agonists may also be readily incorporated into other types of compositions, such as suspensions, viscous or semi-viscous gels, or other types of solid or semi-solid compositions. Suspensions may be preferred for histamine $H_2$ agonists which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the histamine $H_2$ agonists from oxidation during storage. Examples of such antioxidants include vitamin E and analogs thereof, ascorbic acid and butylated hydroxytoluene (BHT).

Ophthalmic products are typically packaged in multidose form. Preservatives are therefore required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye, and thus eliminate or improve the dry eye condition. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any formulation which is safe, and provides the appropriate delivery for the desired route of administration of an effective amount of at least one histamine $H_2$ agonist of the present invention.

The compositions of the present invention are further illustrated by the following examples:

EXAMPLE 3

| Ingredient | Amount (wt %) |
| --- | --- |
| $H_2$ agonist | 0.01–1.0% |
| Phosphate Buffered Saline | 1.0 |
| Polysorbate 80 | 0.5 |
| Purified water | q.s. to 100% |

EXAMPLE 4

| Ingredient | Amount (wt %) |
| --- | --- |
| $H_2$ agonist | 0.01–1.0% |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 5

| Ingredient | Amount (wt %) |
| --- | --- |
| $H_2$ agonist | 0.01–1.0% |
| Phosphate Buffered Saline | 1.0 |
| Hydroxypropyl-β-cyclodextrin | 4.0 |
| Purified water | q.s. to 100% |

The invention in its broader aspects is not limited to the specific details shown and described above. Departures may be made from such details within the scope of the accompanying claims without departing from the principles of the invention and without sacrificing its advantages.

What is claimed is:

1. A method for the treatment of dry eye comprising topically administering to a human patient's eye a composition comprising a pharmaceutically effective amount of one or more histamine $H_2$ agonist(s) in a pharmaceutically acceptable carrier, provided that the one or more histamine $H_2$ agonist(s) does not comprise impromidine.

2. The method of claim 1, wherein the histamine $H_2$ agonist(s) are selected from the group consisting of dimaprit and amthamine.

3. The method of claim 1, wherein the histamine $H_2$ agonist is dimaprit.

4. The method of claim 1, wherein the histamine $H_2$ agonist is amthamine.

* * * * *